US012332918B1

(12) United States Patent
    Altstadter et al.

(10) Patent No.: US 12,332,918 B1
(45) Date of Patent: Jun. 17, 2025

(54) SYSTEMS AND METHODS FOR WEBSITE EMBEDED PORTALS

(71) Applicant: STCHEALTH, LLC, Phoenix, AZ (US)

(72) Inventors: Brandy Altstadter, Scottsdale, AZ (US); Kristen Hutchinson, Bentonville, AR (US); Kristal Shearin, Phoenix, AZ (US); Clark Teeple, Ontario (CA); John Mendez, Mesa, AZ (US)

(73) Assignee: STCHEALTH, LLC, Phoenix, AZ (US)

( * ) Notice: Subject to any disclaimer, the term of this patent is extended or adjusted under 35 U.S.C. 154(b) by 0 days.

(21) Appl. No.: 18/778,597

(22) Filed: Jul. 19, 2024

Related U.S. Application Data

(63) Continuation of application No. 16/414,607, filed on May 16, 2019.

(60) Provisional application No. 62/673,104, filed on May 17, 2018.

(51) Int. Cl.
    *G06F 16/28*     (2019.01)
    *G06F 16/9538*   (2019.01)

(52) U.S. Cl.
    CPC ........ *G06F 16/285* (2019.01); *G06F 16/9538* (2019.01)

(58) Field of Classification Search
    CPC .. G16H 10/60; G06F 16/2291; G06F 16/9538
    USPC ......................................................... 707/737
    See application file for complete search history.

(56) References Cited

U.S. PATENT DOCUMENTS

| | | | |
|---|---|---|---|
| 2007/0150312 A1* | 6/2007 | Schmidt ................. | G06Q 10/10 705/26.1 |
| 2009/0018871 A1* | 1/2009 | Essig .................. | G06Q 30/0236 705/26.1 |
| 2019/0348158 A1* | 11/2019 | Livesay ................ | H04L 9/3239 |

* cited by examiner

*Primary Examiner* — Hung T Vy
(74) *Attorney, Agent, or Firm* — SNELL & WILMER L.L.P.

(57) ABSTRACT

There is a need for a centralized system that enables communication between separate and/or disparate computer systems. The disclosed system, method, and article of manufacture configured to collate datasets between different of computer systems. A portal can be provided that gives access to this collated dataset. Interactions with this GUI can be logged and sent to various computer systems, including those that contributed to the collated dataset.

20 Claims, 4 Drawing Sheets

SYSTEMS AND METHODS FOR WEBSITE EMBEDED PORTALS

CROSS-REFERENCE TO RELATED APPLICATIONS

This is a Continuation of U.S. patent application Ser. No. 16/414,607 filed on May 16, 2019 and entitled "ELECTRONIC HEALTH RECORD AND INVENTORY INTEGRATION," which claims the benefit of U.S. Provisional Patent Application No. 62/673,104, filed May 17, 2018 and entitled "ELECTRONIC HEALTH RECORD AND INVENTORY INTEGRATION," the entire contents of each of which are incorporated by reference herein.

FIELD

The disclosure generally relates to electronic health records, and more specifically, to enabling communication between different electronic health record systems.

BACKGROUND

Immunization levels in the United States are below targeted levels desirable to minimize the incidence of vaccine preventable disease. Additionally, immunization programs typically result in cost savings of 500% or more in direct medical costs as compared to immunization expenses. However, individuals may be unaware of which of their vaccinations are current, and such information may not be readily available to healthcare providers.

Due to the difficulty in obtaining accurate information, in some cases some patients may forego vaccinations which they should receive. In other cases, some patients may unnecessarily duplicate vaccinations.

Employers often wish to host immunization clinics, at which employees may obtain vaccinations. However, for participating healthcare providers, it may be difficult to evaluate which patients require vaccinations, and how much of any given vaccine to bring to the immunization clinic. Additionally, it may be difficult for the healthcare provider, patient, or employer to determine which vaccinations are covered by health insurance.

As such, a need exists for a centralized system which enables communication between separate computer systems in order to identify vaccinations which are covered by insurance, in a healthcare provider's inventory, and due for a patient. Additionally, it would be beneficial if the system were able to facilitate the creation and scheduling of immunization clinics and appointments. Additionally, it would be beneficial for a healthcare provider to quickly identify which vaccinations should be provided to walk-in patients, whether at an immunization clinic or at a pharmacy.

SUMMARY

Many embodiments can include a system. The system can comprise a record management system and a portal generation system. The record management system can comprise at least one processor and at least one tangible, non-transitory memory. The at least one tangible, non-transitory memory can be configured to communicate with the at least one processor and cause the at least one processor to perform querying a first record storage system for a first dataset; querying a second record storage system for a second dataset, wherein the second record storage system is different from the first record storage system; querying each of a first government record data source, a second government record data source, and the second record storage system for a historical dataset of a user; collating the first dataset, the second dataset, and the historical dataset to determine a list of records in the first dataset and the second dataset, but not in the historical dataset of the user; and transmitting the list of records to the portal generation system. The portal generation system can comprise one or more processors and one or more tangible, non-transitory memories. The at least one tangible, non-transitory memories can be configured to communicate with the one or more processors and cause the one or more processors to perform generating an access mechanism for a portal using the list of records; transmitting the access mechanism for the portal to a third computer system; displaying, on a website provided by the third computer system and displayed on a user computer system, the portal comprising a selectable button for each respective data entry in the list of records; receiving, via the portal displayed on the website provided by the third computer system, a selection of a data entry in the list of records; and transmitting the selection of the data entry to the second record storage system.

Various embodiments can include a method. The method can comprise querying, by a record management system, a first record storage system for a first dataset; querying, by the record management system, a second record storage system for a second dataset, wherein the second record storage system is different from the first record storage system; querying, by the record management system, each of a first government record data source, a second government record data source, and the second record storage system for a historical dataset of a user; collating, by the record management system, the first dataset, the second dataset, and the historical dataset to determine a list of records in the first dataset and the second dataset, but not in the historical dataset of the user; transmitting, by the record management system, the list of records to a portal generation system; generating, by the portal generation system, an access mechanism for a portal using the list of records; transmitting, by the portal generation system, the access mechanism for the portal to a third computer system; displaying, by the portal generation system and on a website provided by the third computer system and displayed on a user computer system, the portal comprising a selectable button for each respective data entry in the list of records; receiving, by the portal generation system and via the portal displayed on the website provided by the third computer system, a selection of a data entry in the list of records; and transmitting, by the portal generation system, the selection of the data entry to the second record storage system.

Some embodiments can include one or more articles of manufacture. The one or more articles of manufacture can include one or more non-transitory, tangible computer readable storage mediums. The one or more non-transitory, tangible computer readable storage mediums can have instructions stored thereon that, in response to execution by one or more processors, cause the one or more processors to perform querying, by a record management system, a first record storage system for a first dataset; querying, by the record management system, a second record storage system for a second dataset, wherein the second record storage system is different from the first record storage system; querying, by the record management system, each of a first government record data source, a second government record data source, and the second record storage system for a historical dataset of a user; collating, by the record management system, the first dataset, the second dataset, and the historical dataset to determine a list of records in the first dataset and the second dataset, but not in the historical dataset of the user; transmitting, by the record management system, the list of records to a portal generation system; generating, by the portal generation system, an access mechanism for a portal using the list of records; transmitting, by the portal generation system, the access mechanism for the portal to a third computer system; displaying, by the portal generation system and on a website provided by the third computer system and displayed on a user computer system, the portal comprising a selectable button for each respective data entry in the list of records; receiving, by the portal generation system and via the portal displayed on the website provided by the third computer system, a selection of a data entry in the list of records; and transmitting, by the portal generation system, the selection of the data entry to the second record storage system.

In various embodiments, systems, methods, and articles of manufacture (collectively, "the system") for monitoring and assessing health record data quality are disclosed. The system may perform operations including querying a health insurance provider for covered vaccinations; querying a healthcare provider for vaccinations in an inventory of the healthcare provider; querying a health records data source for due vaccinations for a patient; identifying available vaccinations, wherein the available vaccinations are covered vaccinations, wherein the available vaccinations are in the inventory of the healthcare provider, and wherein the available vaccinations are due vaccinations for the patient; and presenting the available vaccinations to the patient.

In various embodiments, the operations may also comprise receiving a selection of at least one of the available vaccinations; and creating a vaccination appointment for the patient with the healthcare provider. The operations may comprise creating an immunization clinic event for an employer. The vaccination appointment may be part of the immunization clinic event. The system may generate a link to access the immunization clinic event. The vaccinations in the inventory of the healthcare provider may comprise a subset of the covered vaccinations. The due vaccinations may consist of a subset of the vaccinations in the inventory of the healthcare provider. The health records data source may comprise at least one of a state health record data source or a healthcare provider system.

The foregoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may be obtained by referring to the detailed description and claims when considered in connection with the drawing figures, wherein like numerals denote like elements.

DETAILED DESCRIPTION

The detailed description of exemplary embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and/or functional changes may be made without departing from the spirit and scope of the disclosure. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

The present disclosure provides a system, method, and article of manufacture (collectively, "the system") for creating immunization appointments. In a practical application, an employer may request an on-site immunization clinic using the system, or the employer may request that employees receive vaccinations at a pharmacy or similar healthcare provider. The healthcare provider may access a healthcare provider portal to a health records management system. The health records management system may identify which vaccinations are covered by the employer's insurance. The healthcare provider may select vaccinations which the healthcare provide has in inventory. Employees may access a patient portal. The health records management system may verify for which vaccinations the patient is due. The employees may select their desired vaccines. Based on how the employee completes their mandatory consent and/or health history forms, additional vaccines may be recommended based on the self-reported health history information. The health records management system may create appointments for the employees, and the healthcare provider may view the appointments and provide the desired vaccines to the employees.

While the foregoing makes reference to health record data, immunization records, and/or similar such data, it should be recognized by one skilled in the art that the present disclosure may extend to any suitable data processing system wherein reconciling data stored on third party computer systems with available inventory may be desired.

Figure 1:
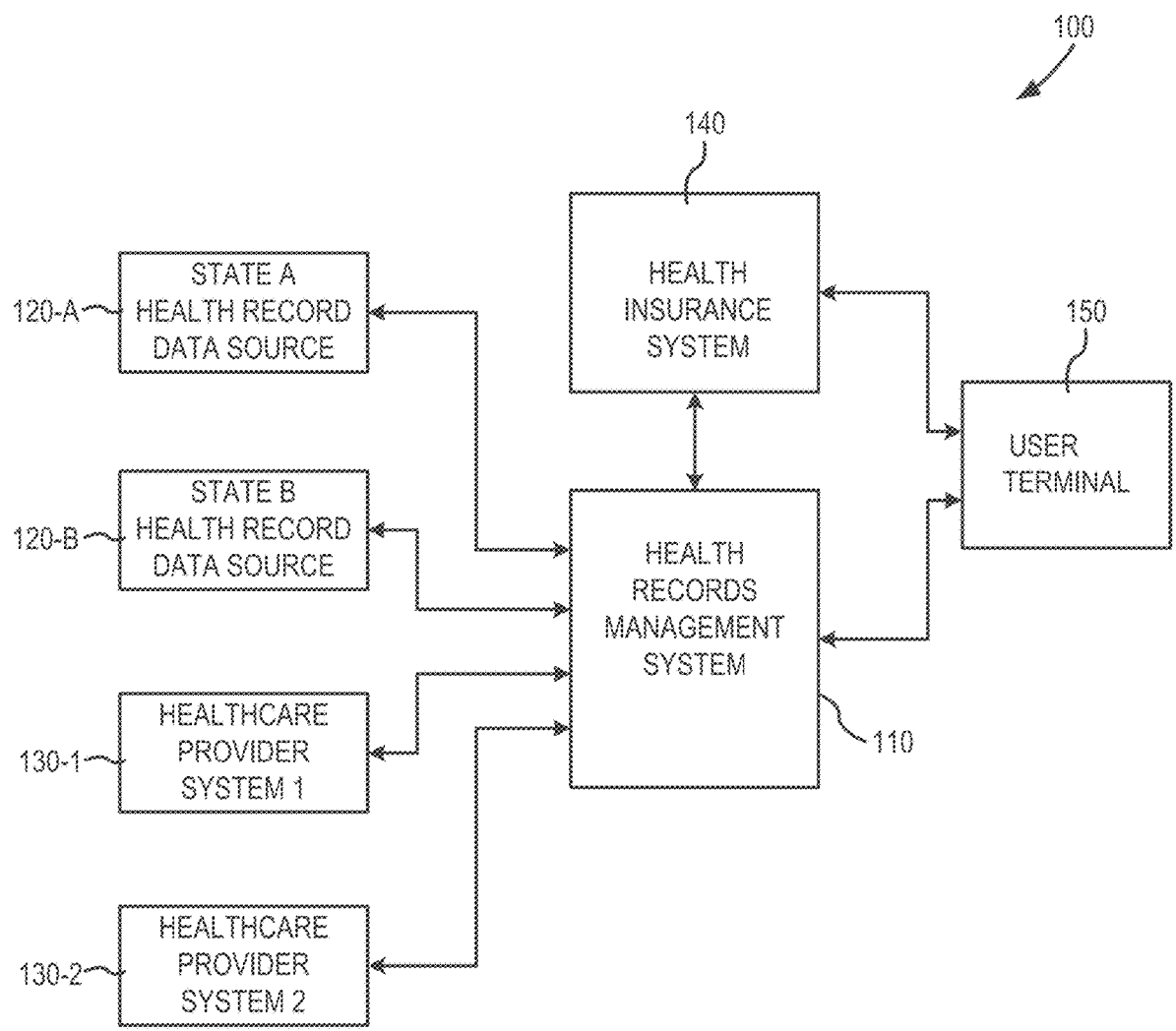
FIG. 1 illustrates a block diagram illustrating various system components of a system for creating immunization appointments, in accordance with various embodiments.

In various embodiments, and with reference to FIG. 1, a system 100 for creating immunization appointments is disclosed. System 100 may be computer based, and may comprise a processor, a tangible non-transitory computer-readable memory, and/or a network interface, along with other suitable system software and hardware components. Instructions stored on the tangible non-transitory memory may allow system 100 to perform various functions, as described herein. System 100 may also contemplate uses in association with web services, utility computing, pervasive and individualized computing, security and identity solutions, autonomic computing, cloud computing, commodity computing, mobility and wireless solutions, open source, biometrics, grid computing and/or mesh computing.

In various embodiments, system 100 may comprise various systems, engines, modules, databases, and components with different roles. The various systems, engines, modules, databases and components described herein may be in direct logical communication with each other via a bus, network, and/or through any other suitable logical interconnection permitting communication amongst the various systems, engines, modules, databases and components, or may be individually connected as described further herein. More specifically, and in accordance with various embodiments, system 100 may comprise one or more of a health records management system 110, a state health record data source (e.g., a state A health record data source 120-A, a state B health record data source 120-B, or the like), a health care provider system (e.g., a healthcare provider system 130-1, a healthcare provider system 130-2, or the like), a health insurance computer system 140, and a user terminal 150.

In various embodiments, health records management system 110 may be in electronic and/or logical communication with one or more state health record data sources (e.g., state A health record data source 120-A, state B health record data source 120-B, or the like), one or more healthcare provider systems (e.g., healthcare provider system 130-1, healthcare provider system 130-2, or the like), health insurance computer system 140, and/or user terminal 150. Health records management system 110 may be configured to facilitate storage and/or transmission of health record data, such as, for example, immunization record data and health history data. Health records management system 110 may be configured to provide a centralized repository for access to vaccine administration records, reminders, vaccination reports, vaccine inventory levels, demand forecasts, or the like. For example, health records management system 110 may be configured to receive health record data from state health record data sources, healthcare provider systems, or the like; parse the health record data to determine the data in the health record data and to detect data quality errors; edit, map, and format the health record data for storage; and store and maintain the health record data in any suitable database (e.g., a health record database), using any suitable technique described herein. Health records management system 110 may comprise any suitable health records management system, such as, for example, the health records management system disclosed in U.S. Ser. No. 14/036,476 titled HEALTH RECORDS MANAGEMENT SYSTEMS AND METHODS and filed on Sep. 25, 2013, the contents of which are herein incorporated by reference in its entirety.

In various embodiments, system 100 may comprise one or more state health record data sources, such as, for example, a state A health record data source 120-A, a state B health record data source 120-B, and/or the like. System 100 may also comprise one or more healthcare provider systems, such as, for example, a healthcare provider system 130-1, a healthcare provider system 130-2, or the like. Each of the state health record data sources 120 and/or the healthcare provider systems 130 may be in electronic and/or logical communication with health records management system 110. Each of the state health record data sources 120 and/or the healthcare provider systems 130 may be configured to transmit health record data to health records management system 110. State health record data sources 120 may comprise any suitable source for health record data, but in various embodiments, the data source is the participating state(s) immunization information system or "registry." The health record data may include health records (e.g., patient information, provider information, medical procedure information, clinical information, diagnostic information, immunization records, prescription information, family information, genetic information, and/or the like), or any other suitable information discussed herein.

Figure 3:
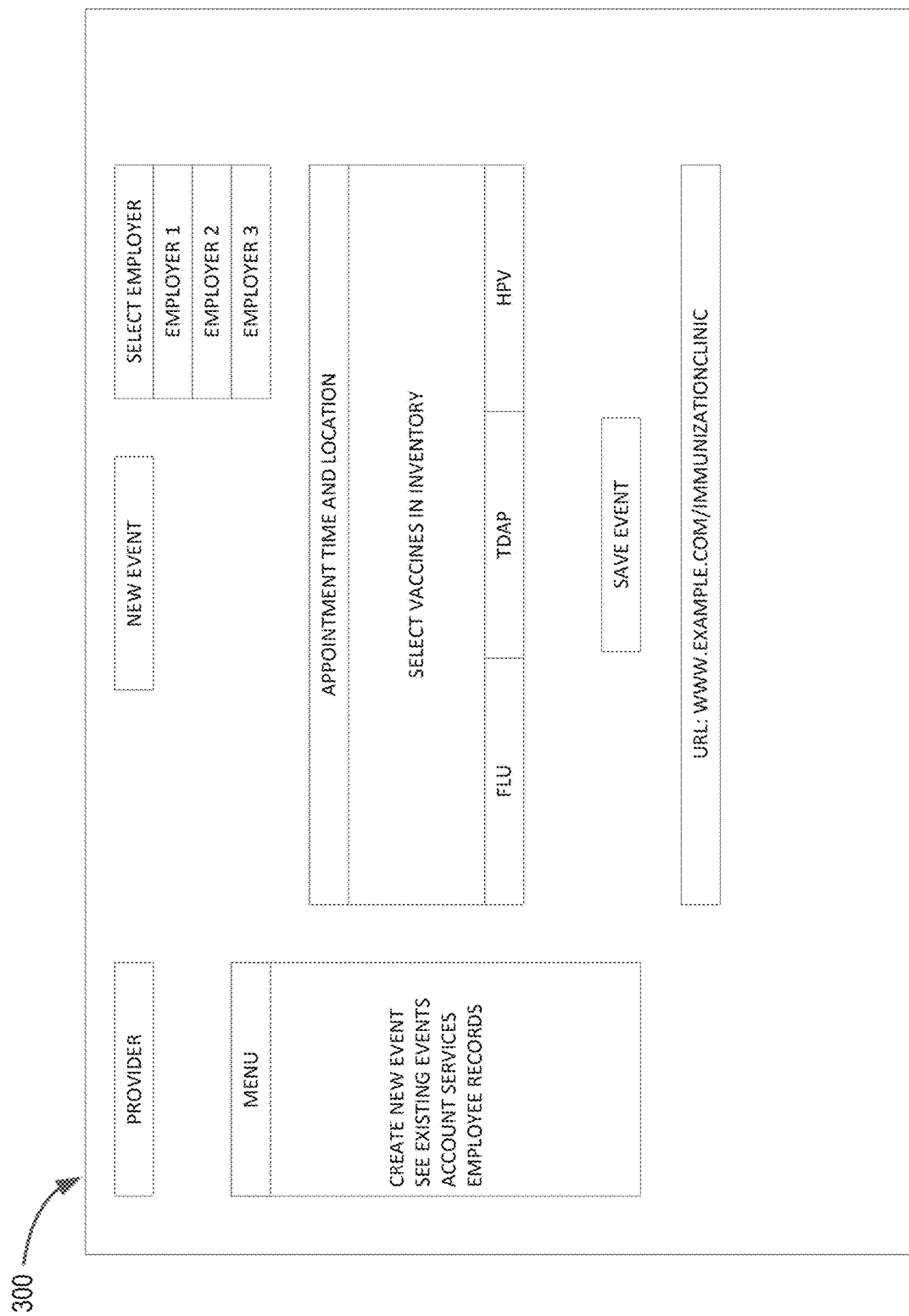
FIG. 3 illustrates a screenshot of a healthcare provider portal for an immunization clinic, in accordance with various embodiments.
Figure 4:
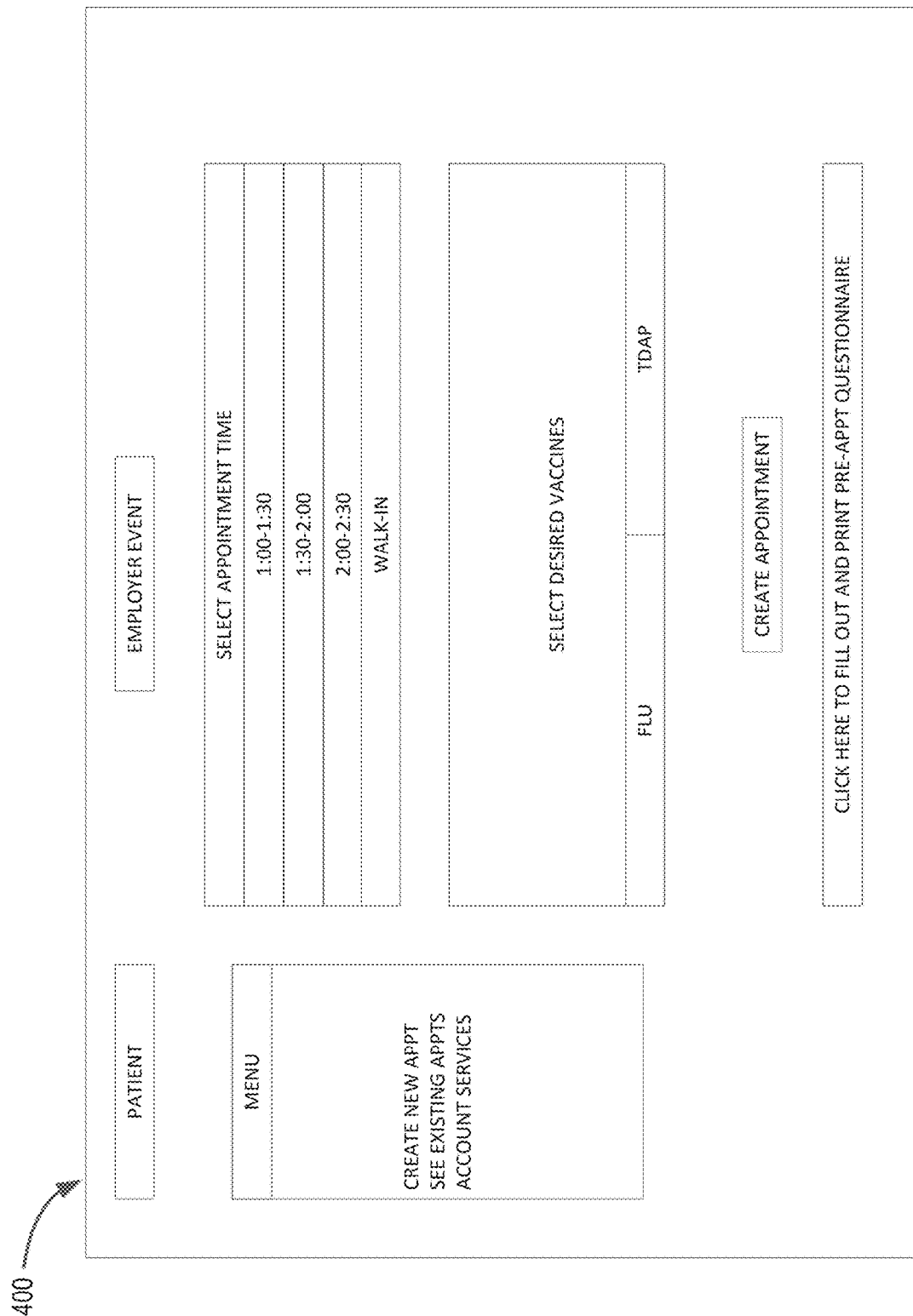
FIG. 4 illustrates a screenshot of a patient portal for an immunization clinic, in accordance with various embodiments.

In various embodiments, user terminal 150 may be in electronic and/or logical communication with health records management system 110 and/or health insurance computer system 140. User terminal 150 may include any device (e.g., a computer, smart phone, tablet, etc.), which communicates, in any manner discussed herein, with health records management system 110 and/or health insurance computer system 140 via any network or protocol discussed herein. Browser applications comprise internet browsing software installed within a computing unit or system to conduct online communications and transactions. These computing units or systems may take the form of personal computers, mobile phones, personal digital assistants, mobile email devices, laptops, notebooks, hand-held computers, portable computers, kiosks, and/or the like. Practitioners will appreciate that user terminal 150 may or may not be in direct contact with health records management system 110 and/or health insurance computer system 140. For example, user terminal 150 may access the services of health records management system 110 through another server, which may have a direct or indirect connection to an internet server. Practitioners will further recognize that user terminal 150 may present interfaces associated with a software application or module that are provided to user terminal 150 via application graphical user interfaces (GUIs) or other interfaces and are not necessarily associated with or dependent upon internet browsers or internet specific protocols (e.g., as depicted in FIGS. 3 and 4). In that regard, a user may interact with user terminal 150 to transmit and receive data, reports, alerts, and the like, as discussed further herein.

Health records management system 110 may provide an immunization clinic portal for healthcare providers, employers, and patients. The portal may allow healthcare providers to create vaccination appointments for employers and patients. In various embodiments, the portal may be hosted by a cloud-based computing system.

In various embodiments, the portal may cross-reference the various system components to identify vaccines which are (1) in the inventory of a healthcare provider; (2) covered by a patient's insurance; (3) due for the patient; and (4) desired by the patient. For example, the portal, via health records management system 110, may communicate with a healthcare provider system (e.g., healthcare provider system 130-1, healthcare provider system 130-2, etc.) to determine the vaccine inventory of a given healthcare provider. The portal, via health records management system 110, may communicate with health insurance computer system 140 to identify and determine the vaccines that are covered by a patient's insurance. The portal, via health records management system 110, may communicate with one or more of a state health record data source (e.g., state A health record data source 120-A, state B health record data source 120-B, etc.), a healthcare provider system (e.g., healthcare provider system 130-1, healthcare provider system 130-2, etc.), a health insurance computer system 140, and/or the patient (e.g., via user terminal 150), to determine and identify the vaccines that are due for the patient. The portal, via health records management system 110, may communicate with the patient, the employer, or the like (e.g., via user terminal 150) to determine the vaccines desired to be received by the patient.

In various embodiments, the portal may also cross-reference the various system components to identify vaccines or recommendations based on the patient's health history. For example, the portal, via health records management system 110, may communicate with one or more of a state health record data source (e.g., state A health record data source 120-A, state B health record data source 120-B, etc.), a healthcare provider system (e.g., healthcare provider system 130-1, healthcare provider system 130-2, etc.), a health insurance computer system 140, and/or the patient (e.g., via user terminal 150), to identify vaccines or recommendations based on received data associated with the patient's health history.

Figure 2:
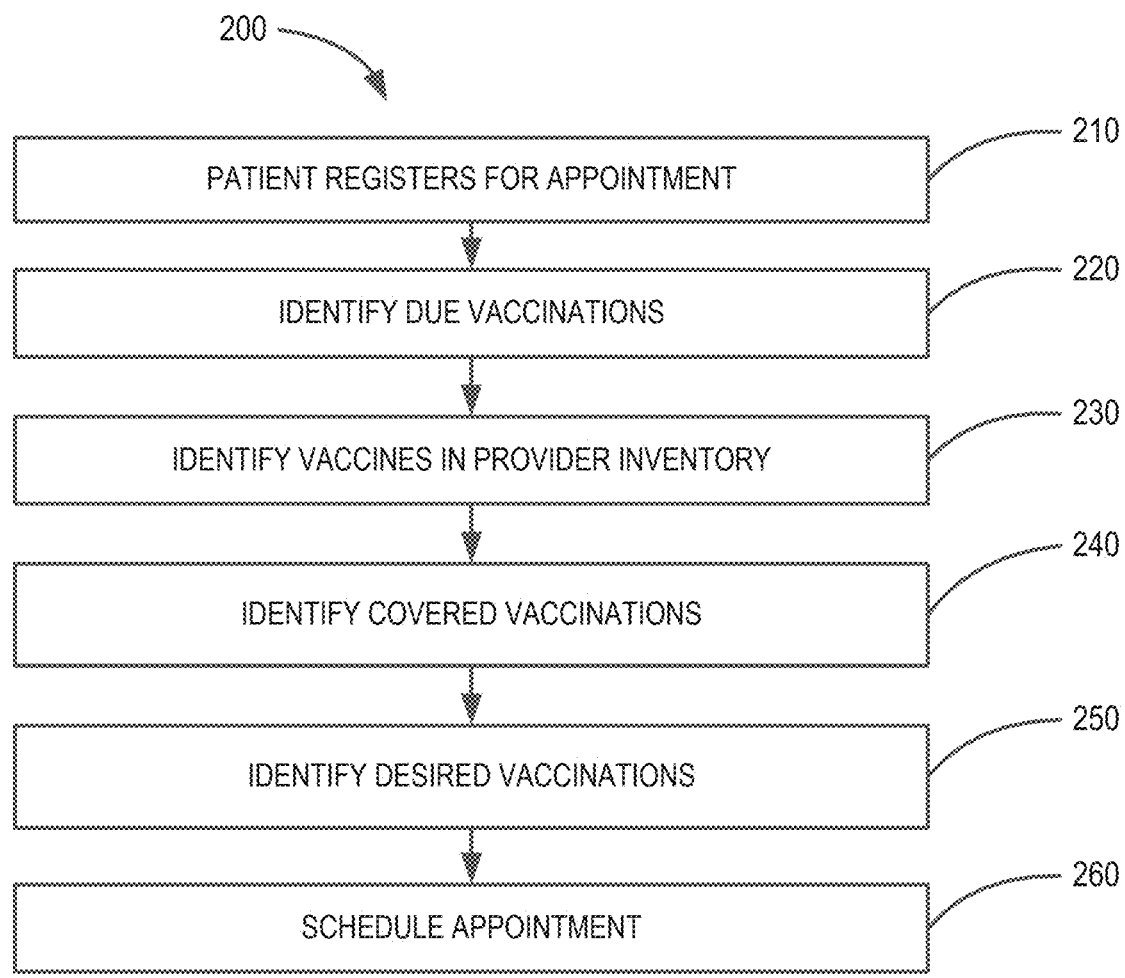
FIG. 2 illustrates a process flow for a method of creating immunization appointments, in accordance with various embodiments.

Referring to FIG. 2, a flowchart of a process 200 for creating a vaccination appointment is illustrated according to various embodiments. A patient may register for a vaccination appointment (step 210). In various embodiments, the patient may register for the vaccination appointment using a personal device, such as a smartphone or personal computer. The patient may create an account with a health records management system, or the patient may login to an existing account with the health records management system. In various embodiments, the patient may register for the vaccination appointment by communicating with a healthcare provider, such as a pharmacist, either over the phone or in person, and the healthcare provider may input patient information to the health records management system. The patient may provide personal information, such as name, date of birth, address, etc. In various embodiments, the patient may also provide an initial reason for the appointment, such as to obtain a flu vaccine.

The health records management system may identify one or more vaccinations for which the patient is due (step 220). In various embodiments, the vaccination records for the patient may be stored by the health records management system. In various embodiments, the health records management system may query a state health record data source for vaccination records for the patient. In various embodiments, the healthcare provider may maintain vaccination records for existing patients of the healthcare provider. Based on the available vaccination records from the various sources, the health records management system may determine which vaccinations the patient is due for. For example, the health records management system may determine that the patient is due for a flu vaccine, a TDAP vaccine (tetanus, diphtheria, and pertussis), an HPV vaccine (human papillomavirus), and a pneumococcal vaccine. In various embodiments, he health records management system may also identify one or more health recommendations based on the patient's health history. For example, based on a history of the patient smoking (e.g., as provided by the patient), the system may recommend that the patient receive a Pneumococcal vaccine or purchase nicotine replacement therapy items.

The health records management system may query the healthcare provider for available vaccine inventory (step 230). In various embodiments, the health records management system may query the healthcare provider computer system, and the healthcare provider computer system may return available vaccine inventory. In various embodiments, a human healthcare provider may input the available vaccine inventory. In various embodiments, the health records management system may only request available inventory for the vaccines for which the patient is due, or for which the system has recommended for the. The healthcare provider may indicate that the healthcare provide has inventory for a subset of the requested vaccines. For example, the healthcare provider may indicate that out of the flu vaccine, the TDAP vaccine, the HPV vaccine, and the pneumococcal vaccine, the healthcare provider may only have inventory for the flu vaccine, the TDAP vaccine, and the HPV vaccine. In various embodiments, in response to a vaccine being unavailable in inventory, the healthcare provider may also return or indicate a date (or date range) that the vaccine will be available. For example, the date (or date range) may be determined based on healthcare provider stocking guidelines, vaccine distributor communications, or the like.

The health records management system may query a health insurance provider to determine which vaccines are covered by the patient's insurance (step 240). As used herein, a covered vaccine refers to any vaccine which the patient may receive for less than full retail price as a result of the patient's health insurance from the health insurance provider. For example, the patient's health insurance may pay or cover a portion of the retail price. As a further example, the patient may receive a rebate, coupon, waiver, discount, or the like in response to purchasing the vaccine. In various embodiment, the health records management system may only request information for the vaccines for which the patient is due and are in the inventory of the healthcare provider. The health insurance provider may indicate that the health insurance provider may only cover a subset of the requested vaccines. For example, the health insurance provider may indicate that the health insurance provider may only cover the flu vaccine and the TDAP vaccine.

The health records management system may query the patient to determine which vaccines the patient would like to receive (step 250). In various embodiments, the health records management system may only present the patient with the option to receive vaccines for which the patient is due, that are covered by the patient's health insurance, and that the healthcare provider has in inventory. The patient may indicate which vaccines they would like to receive. For example, the patient may indicate that the patient would only like to receive the flu vaccine. The health records management system may also query the patient to determine if the patient would like to receive additional items or suggestions based on the patient's healthcare history.

The health records management system may query the various parties in any desired order, or simultaneously. As described with respect to step 210 through step 250, the health records management system may identify (1) vaccinations for which the patient is due; (2) vaccinations covered by insurance; (3) vaccinations in the healthcare provider's inventory; and (4) vaccinations which the patient wishes to receive. However, the health records management system may perform such inquiries in any suitable or desirable order. For example, the health records management system may first identify which vaccinations the patient wishes to receive, then identify which of those vaccinations are covered by insurance, then identify which vaccinations are due, then identify which vaccinations are in the healthcare provider's inventory.

The health records management system may schedule an appointment for the patient to receive the vaccinations (step 260). For a walk-in patient to a healthcare provider, the healthcare provider may simply place the patient into a queue of waiting patients, or if there are no other waiting patients, the patient may receive an immediate appointment. If the patient is registering in advance for the appointment, the patient may select a time and/or location for the appointment, and the health records management may save the appointment time, as well as the planned vaccinations for the appointment. Alternatively, the patient may register ahead of time for a walk-in appointment by completing the form ahead of time, then visiting the healthcare provider at a time convenient to the patient. The patient may print out a form which contains the appointment information, as well as patient information, such as health history, and the patient may bring the form to the appointment in order to expedite the duration of the appointment.

Referring to FIG. 3 a screenshot 300 of a healthcare provider portal for an immunization clinic is illustrated according to various embodiments. An employer may wish to host an immunization clinic. For example, the employer may wish to host the immunization clinic at the employer office, or at a third-party location convenient for employees. Employer hosted immunization clinics may increase vaccination penetration of employees, and in turn decrease health insurance costs and lost productivity due to sick employees.

A healthcare provider may login to a healthcare provider portal to a health records management system. The healthcare provider may enter a login name and password, or the healthcare provider may create a new account. The healthcare provider portal may provide an option to create a new immunization clinic event. The healthcare provider may select an employer. In various embodiments, the healthcare provider may type in an employer name, or select the employer from a drop down list.

The healthcare provider may select a time and location for the immunization clinic. In various embodiments, the employer may have previously requested a specific time and location, and such information may be loaded in response to the healthcare provider selecting the employer. In various embodiments, the healthcare provider may select multiple times and locations for multiple immunization clinics for the employer.

The healthcare provider may define which vaccines the healthcare provider has in inventory for the immunization clinic. The health records management system may have already verified which vaccinations are covered by the employer's health insurance, and the healthcare provider may select from a list of covered vaccines. In various embodiments, the healthcare provider may type in vaccines in inventory, and the health records management system may subsequently verify which vaccines are covered by the employer's insurance, as well as whether additional suggested treatments are covered by the employer's insurance and/or if there is a patient co-payment.

The healthcare provider may select a button to create and save the event. In response to the healthcare provider creating the event, the health records management system may transmit a notification, such as an email, to the employer indicating that the event has been created. In various embodiments, the healthcare provider portal may provide a URL to access the event, and the healthcare provider may transmit the URL to the employer. The healthcare provider may subsequently view a calendar or list of patients which have registered for the immunization clinic, including information such as appointment times and requested vaccines.

In various embodiments, the healthcare provider portal may provide an option to view employee records. The employee records may allow the employer to view which employees have previously received which vaccinations, and whether employees are registered for the immunization clinic.

Referring to FIG. 4, a screenshot 400 of a patient portal for an immunization clinic event is illustrated according to various embodiments. An immunization clinic event may be created, as described with reference to FIG. 3. The employer may notify its employees (also referred to as patients) of the immunization clinic. For example, the employer may email the URL link to the immunization clinic event to the employees. However, in various embodiments, the employees, or members of the general public, may access a patient portal from the employer's website. For example, the employee may visit www.example.com/employer, and the employee may select a button or link to register for the immunization clinic event.

Each employee who wishes to attend the clinic may login to an employee portal to the health records management system. If the employee already has an established account, the employee may enter their login name and address. Otherwise, the employee may create an account by entering additional information.

The employee may select an available time slot for the appointment. In various embodiments, the employee may select a walk-in time slot. The walk-in time slot may allow the employee to visit the immunization clinic event, either at an on-site immunization clinic or at a pharmacy, and the employee may be seen on a space available basis. In various embodiments, at this point the health records management system may identify which vaccinations the employee is due for by querying one or more data sources, as described with reference to FIG. 1 and FIG. 2. The employee may also select which vaccinations the employee would like to receive. The employee may confirm the personal information and create the appointment. In various embodiments, the employee portal may present a pre-visit questionnaire for the employee to fill out. The employee may fill out the questionnaire, and the portal may generate a printable appointment form. The employee may print the appointment form and bring the form to the appointment. The appointment form may include information such as patient identification information, requested vaccines, medical history, etc.

By utilizing the systems and methods herein, patients, healthcare providers, employers, and health insurance companies may streamline the process for patients to receive needed vaccines which are available and covered by health insurance. By streamlining the process, the system may also enable patients to be aware of which of their vaccines are current, and how to receive needed vaccines. The system may reduce the number of patients that may forego vaccinations which they should receive, and also reduce the number of patients that may mistakenly or unnecessarily duplicate vaccinations. In that regard, the system may help increase immunization levels to meet targeted levels desirable to minimize the incidence of vaccine preventable disease.

In various embodiments, the system may therefore provide a technical solution to the technical problem found with typical electronic immunization records. The system enables multiple different systems to interact and share current data in order to provide patients with the proper vaccinations. For example, the system may provide a centralized system and repository that enables communications between state health record data sources, healthcare provider systems, health insurance systems, and employers and patients. As discussed further herein, the centralized system enable the communications between the separate systems in order to identify vaccinations which are covered by insurance, in a healthcare provider's inventory, and/or due or recommended for a patient.

In various embodiments, the system further improves the functioning of the computer-based systems typically involved with electronic immunization records. The system may improve the functioning of the immunization system collectively (e.g., the immunization system) and individually (e.g., each individual system involved in immunization systems). For example, by providing patients and healthcare providers with accurate immunization records, immunization availability, and insurance information, patients, healthcare providers, employees, and similar parties may perform less computer functions and provide less input across the typically separate systems, which saves on data storage and memory and speeds processing across the immunization systems.

Systems, methods and computer program products are provided. In the detailed description herein, references to "various embodiments," "one embodiment," "an embodiment," "an example embodiment," or the like, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "transmit" may include sending at least a portion of electronic data from one system component to another. Additionally, as used herein, "data," "information," or the like may include encompassing information such as commands, queries, files, messages, data for storage, and the like in digital or any other form.

As used herein, "electronic communication" may comprise a physical coupling and/or non-physical coupling capable of enabling system components to transmit and receive data. For example, "electronic communication" may refer to a wired or wireless protocol such as a CAN bus protocol, an Ethernet physical layer protocol (e.g., those using 10BASE-T, 100BASE-T, 1000BASE-T, etc.), an IEEE 1394 interface (e.g., FireWire), Integrated Services for Digital Network (ISDN), a digital subscriber line (DSL), an 802.11a/b/g/n/ac signal (e.g., Wi-Fi), a wireless communications protocol using short wavelength UHF radio waves and defined at least in part by IEEE 802.15.1 (e.g., the BLUETOOTH® protocol maintained by Bluetooth Special Interest Group), a wireless communications protocol defined at least in part by IEEE 802.15.4 (e.g., the ZIGBEE® protocol maintained by the ZigBee alliance), a cellular protocol, an infrared protocol, an optical protocol, or any other protocol capable of transmitting information via a wired or wireless connection.

One or more of the system components may be in electronic communication via a network. As used herein, the term "network" may further include any cloud, cloud computing system, or electronic communications system or method that incorporates hardware and/or software components.

Communication amongst the nodes may be accomplished through any suitable communication channels such as, for example, a telephone network, an extranet, an intranet, Internet, point of interaction device (personal digital assistant, cellular phone, kiosk, tablet, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using Internetwork Packet Exchange (IPX), APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the Internet is generally known to those skilled in the art and, as such, need not be detailed herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

The various system components may be independently, separately or collectively suitably coupled to the network via data links which includes, for example, a connection to an Internet Service Provider (ISP) over the local loop as is typically used in connection with standard modem communication, cable modem, DISH NETWORKS®, ISDN, DSL, or various wireless communication methods. It is noted that the network may be implemented as other types of networks, such as an interactive television (ITV) network. Moreover, the system contemplates the use, sale or distribution of any goods, services or information over any network having similar functionality described herein.

A network may be unsecure. Thus, communication over the network may utilize data encryption. Encryption may be performed by way of any of the techniques now available in the art or which may become available—e.g., Twofish, RSA, El Gamal, Schorr signature, DSA, PGP, PKI, GPG (GnuPG), HPE Format-Preserving Encryption (FPE), Voltage, Triple DES, Blowfish, AES, MD5, HMAC, IDEA, RC6, and symmetric and asymmetric cryptosystems. Network communications may also incorporate SHA series cryptographic methods, elliptic-curve cryptography (e.g., ECC, ECDH, ECDSA, etc.), and/or other post-quantum cryptography algorithms under development.

For the sake of brevity, conventional data networking, application development, and other functional aspects of the system may not be described in detail herein. Furthermore, the connecting lines shown in the various figures contained herein are intended to represent exemplary functional relationships and/or electronic communications between the various elements. It should be noted that many alternative or additional functional relationships or electronic communications may be present in a practical system.

As used herein, "meet," "match," "associated with," or similar phrases may include an identical match, a partial match, meeting certain criteria, matching a subset of data, a correlation, satisfying certain criteria, a correspondence, an association, an algorithmic relationship and/or the like. Similarly, as used herein, "authenticate" or similar terms may include an exact authentication, a partial authentication, authenticating a subset of data, a correspondence, satisfying certain criteria, an association, an algorithmic relationship and/or the like.

Terms and phrases similar to "associate," "associating," or the like may include tagging, flagging, correlating, using a look-up table or any other method or system for indicating or creating a relationship between data elements. Moreover, the associating may occur at any point, in response to any suitable action, event, or period of time. The associating may occur at pre-determined intervals, periodic, randomly, once, more than once, or in response to a suitable request or action. Any of the information may be distributed and/or accessed via a software enabled link, wherein the link may be sent via an email, text, post, social network input and/or any other method known in the art.

Any communication, transmission and/or channel discussed herein may include any system or method for delivering content (e.g., health record data, data, information, metadata, etc.), and/or the content itself. The content may be presented in any form or medium, and in various embodiments, the content may be delivered electronically and/or capable of being presented electronically. For example, a channel may comprise a website, mobile application, or device (e.g., FACEBOOK®, YOUTUBE®, PANDORA®, APPLE TV®, MICROSOFT® XBOX®, ROKU®, AMAZON FIRE®, GOOGLE CHROMECAST™, SONY® PLAYSTATION®, NINTENDO® SWITCH®, etc.) a uniform resource locator ("URL"), a document (e.g., a MICROSOFT® Word™ or EXCEL®, an ADOBE® Portable Document Format (PDF) document, etc.), an "eBook," an "eMagazine," an application or micro-application (as described herein), an SMS or other type of text message, an email, a FACEBOOK® message, a TWITTER® tweet, multimedia messaging services (MMS), and/or other type of communication technology. In various embodiments, a channel may be hosted or provided by a data partner. In various embodiments, the distribution channel may comprise at least one of a state data source website, a healthcare provider website, a social media website, affiliate or partner websites, an external vendor, a mobile device communication, social media network and/or location based service. Distribution channels may include at least one of a healthcare provider website, a social media site, affiliate or partner websites, an external vendor, and/or a mobile device communication. Examples of social media sites include FACEBOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, QZONE®, WECHAT®, and the like. Moreover, examples of mobile device communications include texting, email, and mobile applications for smartphones.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include health record data and/or data useful in the operation of the system. As those skilled in the art will appreciate, user computer may include an operating system (e.g., WINDOWS®, UNIX®, LINUX®, SOLARIS®, MACOS®, etc.) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations or any of the operations may be conducted or enhanced by artificial intelligence (AI) or machine learning. Artificial intelligence may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In fact, in various embodiments, the embodiments are directed toward one or more computer systems capable of carrying out the functionality described herein. The computer system includes one or more processors. The processor is connected to a communication infrastructure (e.g., a communications bus, cross over bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

The terms "computer program medium," "computer usable medium," and "computer readable medium" may be used to generally refer to media such as removable storage drive and a hard disk installed in hard disk drive. These computer program products provide software to computer system.

Computer programs (also referred to as computer control logic) are stored in main memory and/or secondary memory. Computer programs may also be received via communications infrastructure. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into computer system using removable storage drive, hard disk drive or communications interface. The control logic (software), when executed by the processor, causes the processor to perform the functions of various embodiments as described herein. Implementation of the hardware so as to perform the functions described herein will be apparent to persons skilled in the relevant art(s).

In various embodiments, the server may include application servers (e.g., WEBSPHERE®, WEBLOGIC®, JBOSS®, POSTGRES PLUS ADVANCED SERVER®, etc.). In various embodiments, the server may include web servers (e.g., Apache, IIS, GOOGLE® Web Server, SUN JAVA® System Web Server, JAVA® Virtual Machine running on LINUX® or WINDOWS® operating systems).

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various conventional support software and drivers typically associated with computers. The web-client may also run MICROSOFT® INTERNET EXPLORER® software, MOZILLA® FIREFOX® software, GOOGLE® CHROME® software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

In various embodiments, components, modules, and/or engines of the system may be implemented as micro-applications or micro-apps. Micro-apps are typically deployed in the context of a mobile operating system, including for example, a WINDOWS® mobile operating system, an ANDROID® operating system, an APPLE® iOS operating system, a BLACKBERRY® company's operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Common database products that may be used to implement the databases include DB2® by IBM® (Armonk, NY), various database products available from ORACLE® Corporation (Redwood Shores, CA), MICROSOFT ACCESS® or MICROSOFT SQL SERVER® by MICROSOFT® Corporation (Redmond, Washington), MYSQL® by MySQL AB (Uppsala, Sweden), MONGODB®, Redis, Apache Cassandra®, HBASE® by APACHE®, MapR-DB by the MAPR® corporation, or any other suitable database product. Moreover, any database may be organized in any suitable manner, for example, as data tables or lookup tables. Each record may be a single file, a series of files, a linked series of data fields, or any other data structure.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

As stated above, in various embodiments, the data can be stored without regard to a common format. However, the data set (e.g., BLOB) may also be annotated in a standard manner. The annotation may comprise a short header, trailer, or other appropriate indicator related to each data set that is configured to convey information useful in managing the various data sets. For example, the annotation may be called a "condition header," "header," "trailer," or "status," herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the access levels. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

One skilled in the art will also appreciate that, for security reasons, any databases, systems, devices, servers, or other components of the system may consist of any combination thereof at a single location or at multiple locations, wherein each database, system, device, server, and/or other component includes any of various suitable security features, such as firewalls, access codes, encryption, decryption, compression, decompression, and/or the like.

The computing unit of the web client may be further equipped with an Internet browser connected to the Internet or an intranet using standard dial-up, cable, DSL or any other Internet protocol known in the art. Communications originating at a web client may pass through a firewall in order to prevent unauthorized access from users of other networks. Further, additional firewalls may be deployed between the varying components of CMS to further enhance security.

The computers discussed herein may provide a suitable website or other Internet-based graphical user interface which is accessible by users. In one embodiment, the MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. For example, representational state transfer (REST), or RESTful, web services may provide one way of enabling interoperability between applications.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the internet server. Middleware may be configured to process transactions between the various components of an application server and any number of internal or external systems for any of the purposes disclosed herein. WEBSPHERE® MQ™ (formerly MQSeries) by IBM®, Inc. (Armonk, NY) is an example of a commercially available middleware product. An Enterprise Service Bus ("ESB") application is another example of middleware.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT®, JAVASCRIPT® Object Notation (JSON), VBScript, Macromedia COLD FUSION, COBOL, MICROSOFT® company's Active Server Pages, assembly, PERL®, PHP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT®, VBScript, or the like.

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, BLU-RAY DISC®, optical storage devices, magnetic storage devices, and/or the like.

The system and method(s) is described herein with reference to screen shots, block diagrams, and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS® applications, webpages, websites, web forms, prompts, etc. Practitioners will appreciate that the illustrated steps described herein may comprise in any number of configurations including the use of WINDOWS® applications, webpages, web forms, popup WINDOWS® applications, prompts, and the like. It should be further appreciated that the multiple steps as illustrated and described may be combined into single webpages and/or WINDOWS® applications but have been expanded for the sake of simplicity. In other cases, steps illustrated and described as single process steps may be separated into multiple webpages and/or WINDOWS® applications but have been combined for simplicity.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In re Nuijten to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. § 112 (f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system comprising
a record management system comprising at least one processor and at least one tangible, non-transitory memory configured to communicate with the at least one processor and cause the at least one processor to perform:
  querying a first record storage system for a first dataset;
  querying a second record storage system for a second dataset, wherein the second record storage system is different from the first record storage system;
  querying each of a first government record data source, a second government record data source, and the second record storage system for a historical dataset of a user;
  collating the first dataset, the second dataset, and the historical dataset to determine a list of records in the first dataset and the second dataset, but not in the historical dataset of the user; and
  transmitting the list of records to a portal generation system; and
the portal generation system comprising one or more processors and one or more tangible, non-transitory memories configured to communicate with the one or more processors and cause the one or more processors to perform:
  transmitting the list of records to the second record storage system;
  receiving, from the second record storage system, a proposed list of dates and a proposed list of locations, wherein at least a portion of the proposed list of dates are determined by stock guidelines stored on the second record storage system and communications from distributors;
  generating an access mechanism for a portal using the list of records, the proposed list of dates, and the proposed list of locations;
  transmitting the access mechanism for the portal to a third computer system;
  displaying, on a website provided by the third computer system and displayed on a user computer system, the portal comprising a respective selectable button for each respective date in the at least the portion of the proposed list of dates;

receiving, via the portal displayed on the website provided by the third computer system, a selection of the at least one respective button; and transmitting the selection of the selection to the second record storage system.

2. The system of claim 1 wherein the at least one tangible, non-transitory memory is further configured to cause the at least one processor to perform:

formatting each of the queries to the first government record data source and the second government record data source into a common format.

3. The system of claim 2 wherein the common format comprises Health Level 7 (HL7) format.

4. The system of claim 1 wherein the portal comprises a user facing GUI generated by the portal generation system.

5. The system of claim 1 wherein the one or more tangible, non-transitory memories are further configured to cause the one or more processors to perform:

in response to receiving the selection, transmitting a notification to the third computer system indicating the selection.

6. The system of claim 1 wherein the one or more tangible, non-transitory memories are further configured to cause the one or more processors to perform:

transmitting, to the second record storage system, a second access mechanism for a second portal; and coordinating displaying on the second record storage system, and via the second portal, a list of unselected data entries from the list of records.

7. The system of claim 1 wherein the at least one tangible, non-transitory memory is further configured to cause the at least one processor to perform:

before displaying the portal on the website, mapping the first dataset, the second dataset, and the historical dataset to a format used for centralized storage.

8. A method comprising:

querying, by a record management system, a first record storage system for a first dataset;

querying, by the record management system, a second record storage system for a second dataset, wherein the second record storage system is different from the first record storage system;

querying, by the record management system, each of a first government record data source, a second government record data source, and the second record storage system for a historical dataset of a user;

collating, by the record management system, the first dataset, the second dataset, and the historical dataset to determine a list of records in the first dataset and the second dataset, but not in the historical dataset of the user;

transmitting, by the record management system, the list of records to a portal generation system;

transmitting, by the portal generation system, the list of records to the second record storage system;

receiving, at the portal generation system and from the second record storage system, a proposed list of dates and a proposed list of locations, wherein at least a portion of the proposed list of dates are determined by stock guidelines stored on the second record storage system and communications from distributors;

generating, by the portal generation system, an access mechanism for a portal using the list of records, the proposed list of dates, and the proposed list of locations;

transmitting, by the portal generation system, the access mechanism for the portal to a third computer system;

displaying, by the portal generation system and on a website provided by the third computer system and displayed on a user computer system, the portal comprising a respective selectable button for each respective date in the at least the portion of the proposed list of dates;

receiving, by the portal generation system and via the portal displayed on the website provided by the third computer system, a selection of the at least one respective button; and transmitting, by the portal generation system, the selection of the selection to the second record storage system.

9. The method of claim 8 further comprising:

formatting, by the record management system, each of the queries to the first government record data source and the second government record data source into a common format.

10. The method of claim 9 wherein the common format comprises Health Level 7 (HL7) format.

11. The method of claim 8 wherein the portal comprises a user facing GUI generated by the portal generation system.

12. The method of claim 8 further comprising:

in response to receiving the selection, transmitting, by the portal generation system, a notification to the third computer system indicating the selection.

13. The method of claim 8 further comprising:

transmitting, by the portal generation system to the second record storage system, a second access mechanism for a second portal; and coordinating displaying, by the portal generation system, on the second record storage system, and via the second portal, a list of unselected data entries from the list of records.

14. The method of claim 8 further comprising:

before displaying the portal on the website, mapping, by the record management system, the first dataset, the second dataset, and the historical dataset to a format used for centralized storage.

15. One or more articles of manufacture including one or more non-transitory, tangible computer readable storage mediums having instructions stored thereon that, in response to execution by one or more processors, cause the one or more processors to perform:

querying, by a record management system, a first record storage system for a first dataset;

querying, by the record management system, a second record storage system for a second dataset, wherein the second record storage system is different from the first record storage system;

querying, by the record management system, each of a first government record data source, a second government record data source, and the second record storage system for a historical dataset of a user;

collating, by the record management system, the first dataset, the second dataset, and the historical dataset to determine a list of records in the first dataset and the second dataset, but not in the historical dataset of the user;

transmitting, by the record management system, the list of records to a portal generation system;

transmitting, by the portal generation system, the list of records to the second record storage system;

receiving, at the portal generation system and from the second record storage system, a proposed list of dates and a proposed list of locations, wherein at least a portion of the proposed list of dates are determined by stock guidelines stored on the second record storage system and communications from distributors;

generating, by the portal generation system, an access mechanism for a portal using the list of records, the proposed list of dates, and the proposed list of locations;

transmitting, by the portal generation system, the access mechanism for the portal to a third computer system;

displaying, by the portal generation system and on a website provided by the third computer system and displayed on a user computer system, the portal comprising a respective selectable button for each respective date in the at least the portion of the proposed list of dates;

receiving, by the portal generation system and via the portal displayed on the website provided by the third computer system, a selection of the at least one respective button; and transmitting, by the portal generation system, the selection of the selection to the second record storage system.

16. The one or more articles of manufacture of claim 15 further comprising:

formatting, by the record management system, each of the queries to the first government record data source and the second government record data source into a common format.

17. The one or more articles of manufacture of claim 16, wherein the common format comprises Health Level 7 (HL7) format.

18. The one or more articles of manufacture of claim 15, wherein the portal comprises a user facing GUI generated by the portal generation system.

19. The one or more articles of manufacture of claim 15, wherein the one or more non-transitory, tangible computer readable storage mediums are further configured to cause the one or more processors to perform:

in response to receiving the selection, transmitting, by the portal generation system, a notification to the third computer system indicating the selection.

20. The one or more articles of manufacture of claim 15, wherein the one or more non-transitory, tangible computer readable storage mediums are further configured to cause the one or more processors to perform:

transmitting, by the portal generation system to the second record storage system, a second access mechanism for a second portal; and coordinating displaying, by the portal generation system, on the second record storage system, and via the second portal, a list of unselected data entries from the list of records.

* * * * *